US00RE34984E

United States Patent [19]

Kitao et al.

[11] E Patent Number: Re. 34,984

[45] Reissued Date of Patent: Jun. 27, 1995

[54] NYLON COMPOSITION HAVING INCREASED HYDROYLZABILITY AND METHOD FOR INCREASING HYDROLYZABILITY OF NYLON

[75] Inventors: Toshio Kitao, Kyoto; Yoshiharu Kimura, Ohmihachiman; Hideki Yamane; Hiroki Nakata, both of Kyoto; Hosei Shinoda, Kasugai, all of Japan

[73] Assignee: Mitsui Toatsu Chemicals, Inc., Tokyo, Japan

[21] Appl. No.: 224,301

[22] Filed: Apr. 7, 1994

Related U.S. Patent Documents

Reissue of:

[64] Patent No.: 5,272,221
Issued: Dec. 21, 1993
Appl. No.: 863,085
Filed: Apr. 3, 1992

[30] Foreign Application Priority Data

Apr. 9, 1991 [JP] Japan ..... 3-076011
Sep. 30, 1991 [JP] Japan ..... 3-250699

[51] Int. Cl.[6] ..... G08G 69/48; C08L 77/00

[52] U.S. Cl. ..... 525/420; 525/411; 525/178; 525/937

[58] Field of Search ..... 525/411, 178, 420, 937

[56] References Cited

U.S. PATENT DOCUMENTS 4,343,931 10/1982 Barrows ..... 528/291
5,013,315 5/1991 Barrows ..... 606/71

FOREIGN PATENT DOCUMENTS 05192 2/1943 Japan .
36597 10/1974 Japan .
82865 5/1984 Japan .
164718 7/1987 Japan .
164726 7/1987 Japan .
500076 1/1988 Japan .
47731 9/1988 Japan .

*Primary Examiner*—James J. Seidleck
*Assistant Examiner*—I. Zemel
*Attorney, Agent, or Firm*—Burns, Doane, Swecker & Mathis

[57] ABSTRACT

The present invention provides a nylon composition having increased hydrolyzability which is obtained by physically mixing 100 parts by weight of a nylon with 1 to 50 parts by weight of at least one polymer selected from the group consisting of polylactic acid, polyglycolic acid and a copolymer containing 50 mol % or more of a lactic acid unit or a glycolic acid unit as a repeating unit in its chain; and a method for increasing the hydrolyzability of a nylon by preparing such a composition. High hydrolyzability can be imparted to the nylon inherently having extremely low hydrolyzability without impairing its original mechanical strength. Therefore, various molded articles made from the nylon can be hydrolyzed under natural circumstances, and thus the wastes are not stored.

9 Claims, No Drawings

NYLON COMPOSITION HAVING INCREASED HYDROYLZABILITY AND METHOD FOR INCREASING HYDROLYZABILITY OF NYLON

Matter enclosed in heavy brackets [ ] appears in the original patent but forms no part of this reissue specification; matter printed in italics indicates the additions made by reissue.

BACKGROUND OF THE INVENTION (i) Field of the Invention

The present invention relates to a nylon composition having increased hydrolyzability and a method for increasing the hydrolyzability of a nylon.

(ii) Description of the Prior Art

Nylons are produced in large quantities on an industrial scale and utilized in many occasions of daily lives, because of being excellent in wear resistance, toughness, chemical resistance, heat resistance, cold resistance and moldability.

As widely known, however, it is difficult to decompose the nylons under natural circumstances. Therefore, when various kinds of materials and molded articles made from nylons because unnecessary and are disposed without burning them, they are stored as waste for a long period of time. The amount of the waste remarkably increases with the development of industry, which is a serious social problem nowadays in the world.

If the hydrolyzability of the nylons can be increased, this will be a means effective to solve the above-mentioned problem. That is, if the various kinds of materials and molded articles made from nylon are disposed of after the period of use, and their weight, volume, strength and the like are then decreased or deteriorated by rapid hydrolysis. This will largely contribute to the protection of the environment.

Nevertheless, there have been found neither a nylon composition which can be effectively hydrolyzed under the natural circumstances nor a method for imparting, to the nylons, characteristics by which they can be effectively hydrolyzed under natural circumstances.

For example, Japanese Patent National Publication (Kohyo) No. 500076/1988 (PCT/US 86/01168; the fundamental application of the priority in U.S. Ser. No. 754870, now U.S. Pat. No. 5,013,315) discloses a bone plate spacer made from a resin composition containing an unabsorbable polymer and an absorbable polymer.

As the unabsorbable polymer which can be preferably used in the bone plate spacer, polyurethanes, polyalkylenes and nylons are disclosed, and as the absorbable polymer, polyesteramides, polyglycolic acid, polylactic acid, polydioxanone, polytrimethylene carbonate and the like are disclosed.

However, this patent publication separately discloses the nylon which is an unabsorbable polymer as well as the polyglycolic acid, the polyactic acid, a glycolic acid compolymer and a lactic acid copolymer which are the absorbable polymers, and it does not reveal any embodiments regarding pairs of the nylon and the polyglycolic acid, the nylon and the polylactic acid, the nylon and the glycolic acid copolymer, and the nylon and the lactic acid copolymer.

Accordingly, the unabsorbable polymer constituting the bone plate spacer disclosed in the patent publication still tenaciously remains undecomposed in an elastic state, after the absorbable polymer has been absorbed.

As is apparent from the foregoing, there have been known neither the nylon composition which can be effectively hydrolyzed under natural circumstances nor the method for imparting, to the nylon, characteristics by which they can be effectively hydrolyzed under the natural circumstances.

SUMMARY OF THE INVENTION

An object of the present invention is to provide a nylon composition which can solve the above-mentioned problem and to which high hydrolyzability is imparted without impairing the advantageous characteristics inherent in the nylon.

Another object of the present invention is to provide a method for imparting high hydrolyzability to a nylon composition.

The above-mentioned objects of the present invention can be achieved by providing a first invention, i.e., a nylon composition having increased hydrolyzability which is obtained by physically mixing 100 parts by weight of a nylon with 1 to 50 parts by weight of at least one selected from the group consisting of polylactic acid, polyglycolic acid and a copolymer containing 50 mol % or more of a lactic acid unit or a glycolic acid unit as a repeating unit in its chain and a second invention, i.e., a method for increasing the hydrolyzability of a nylon which comprises the step of physically mixing 100 parts by weight of a nylon with 1 to 50 parts by weight of at least one selected from the group consisting of polylactic acid, polyglycolic acid and a copolymer containing 50 mol % or more of a lactic acid unit or a glycolic acid unit as a repeating unit in its chain.

That is, the present invention has been completed on the basis of the knowledge that a nylon is effectively hydrolyzed by physically blending the nylon with a specific amount of polylactic acid, polyglycolic acid, a lactic acid copolymer or a glycolic acid copolymer having a specific composition.

According to the present invention, high hydrolyzability can be imparted to the nylon or its composition having inherently extremely low hydrolyzability without imparting its original mechanical strength, or the hydrolyzability or the nylon or its composition can be increased. Therefore, in the case that articles of the nylon which will be used in throwaway applications are molded, a composition obtaining by mixing the nylon with the lactic acid polymer or the glycolic acid polymer is to be molded. Furthermore, in the case that articles of the nylon which can be used in durable applications are molded, the nylon or its composition is to be molded without mixing the lactic acid polymer or the glycolic acid polymer, and prior to disposing of the articles, the molded articles of the nylon are melted and mixed with the lactic acid polymer of the glycolic acid polymer and afterward they can be thrown away.

Thus, if the nylon composition of the present invention or the molded articles of the nylon obtained by applying the method of the present invention are disposed of, the composition or the articles are hydrolyzed in a relatively short time together with the lactic acid polymer or the glycolic acid polymer under the natural circumstances. In consequence, the nylon composition or the nylon articles are not stored any more as industrial wastes, and they are very useful for the treatment of the industrial wastes.

DESCRIPTION OF THE PREFERRED EMBODIMENTS

A nylon referred to in the present invention means a polyamide having an amide bond in its molecular structure or a resin composition containing the polyamide as the main component, i.e., a polyamide series polymer (hereinafter referred to as "nylon") which is not easily hydrolyzed under natural circumstances. Typical examples of the nylon include nylons such as 6-nylon, 6,6-nylon, 6,10-nylon, 11-nylon and 12-nylon, aromatic polyamides and blends of these nylons. Above all, 6-nylon and 6,6-nylon are preferable, and 6-nylon is particularly preferable. No particular restriction is put on the molecular weight of the nylon.

In the present invention, polylactic acid which will be mixed with the nylon can be obtained by subjecting lactic acid to dehydration polycondensation, preferably by subjecting lactide, which is a cyclic dimer of lactic acid, to a ring opening polymerization.

In lactic acid, two kinds of optical isomers, i.e., L-lactic acid and D-lactic acid are present. Furthermore, in lactide, there are L-lactide which is a cyclic dimer of L-lactic acid, D-lactic which is a cyclic dimer of D-lactic acid, meso-lactide which is a cyclic dimer of D-lactic acid and L-lactic acid, and DL-lactide which is a racemic mixture of D-lactide and L-lactide. In the present invention, any lactic acid or any lactide can be used.

Polyglycolic acid which can be mixed with the nylon can be obtained by subjecting glycolic acid to dehydration polycondensation, preferably by subjecting glycolide, which is a cyclic dimer of glycolic acid, to a ring opening polymerization.

In the present invention, examples of a lactic acid copolymer containing 50 mol % or more of a lactic acid unit which is mixed with the nylon include lactic acid-glycolic acid copolymer, lactic acid-hydrocaproic acid copolymer, lactic acid-hydroxybutyric acid copolymer, lactic acid-hydroxyvaleric acid copolymer, lactic acid-p-dioxanone copolymer and lactic acid-trimethylene carbonate copolymer.

Furthermore, in the present invention, examples of a glycolic acid copolymer containing 50 mol % or more of a glycolic acid unit which is mixed with the nylon include lactic acid-glycolic acid copolymer, glycolic acid-hydroxycaproic acid copolymer, glycolic acid-hydroxybutyric acid copolymer, glycolic acid-hydroxyvaleric acid copolymer, glycolic acid-p-dioxanone copolymer and glycolic acid-trimethylene carbonate copolymer.

Each of these copolymers contains 50 mol % or more of the lactic acid unit or the glycolic acid unit as a repeating unit in its chain.

When the amount of the lactic acid unit or the glycolic acid unit is less than 50 mol %, it is necessary that the amount of the copolymer is as much as 50 parts by weight to the nylon in order to effectively increase the hydrolyzability of the nylon. In that case, the large amount of the copolymer unpreferably impairs the mechanical properties, heat resistance and chemical resistance, which the nylon itself inherently has.

No particular restriction is put on the molecular weight of the polylactic acid or the lactic acid copolymer which is used in the present invention, but its preferable weight average molecular weight is 700,000 or less. When the molecular weight of the lactic acid polymer is too high, the mixing of the polymer with the nylon is difficult, and the hydrolyzability of the nylon cannot be increased sufficiently. More preferably, the weight average molecular weight of the polymer is in the range of 150 to 700,000, and most preferably, it is in the range of 150 to 100,000.

Furthermore, no particular restriction is put on the molecular weight of the polyglycolic acid or the glycolic acid copolymer which is used in the present invention, but when the molecular weight of the glycolic acid polymer is too high, it is difficult to mix the polymer with the nylon, and the hydrolyzability of the nylon cannot be increased sufficiently. The weight average molecular weight of the polymer is preferably less than 200,000, more preferably in the range of 150 to 200,000, and most preferably, 150 to 100,000.

The above-mentioned polylactic acid, lactic acid copolymer, polyglycolic acid and glycolic acid copolymer can be obtained by known synthetic methods. For example, the polylactic acid or the polyglycolic acid can be each obtained by the dehydration polycondensation of lactic acid or glycolic acid, or the ring opening polymerization of lactic or glycolide, as disclosed in Japanese Patent Publication Nos. 5192/1968 and 36597/1974.

Moreover, the glycolic acid-hydroxycaproic acid copolymer can be obtained by polymerizing a mixture of glycolide and $\epsilon$-caprolactone at 195° C. in the presence of stannous octoate as a catalyst, as disclosed in Japanese Patent Application Laid-open No. 82865/1984.

The copolymer of lactic acid and p-dioxanone as well as the copolymer of glycolic acid and p-dioxanone can be obtained in accordance with methods for preparing p-dioxanone-lactide copolymer or p-dioxanone-glycolide copolymer, as disclosed in Japanese Patent Application Laid-open Nos. 164718/1987 and 164726/1987, respectively. For example, a method is usable which comprises reacting p-dioxanone at room temperature and 110° C. in the presence of 1-dodecanol and stannous octoate, adding L-lactide thereto, and then further carrying out reaction at 125° C.

The copolymer of lactic acid and trimethylene carbonate can be obtained by reacting trimethylene carbonate at 180° C. in the presence of stannous chloride and lauryl alcohol, adding lactide thereto, and then further carrying out reaction at 223° C., as disclosed in Japanese Patent Publication No. 47731/1988.

In addition, the lactic acid polymer or the glycolic acid polymer which can be used in the present invention can be synthesized, for example, by copolymerizing lactide or glycolide with another lactone such as $\beta$-propiolactone, $\delta$-valerolactone or octanolactone.

In the present invention, "physically mixing the nylon with the polylactic acid, the polyglycolic acid or the copolymer containing 50 mol % or more of the lactic acid unit or the glycolic acid unit as the repeating unit in its chain (hereinafter referred to as "lactic acid polymer" or "glycolic acid polymer") means that an ester-amide exchange reaction does not substantially occur between the nylon and the lactic acid polymer or the glycolic acid polymer, when they are mixed. If the ester-amide exchange occurs between the nylon and the lactic acid polymer or the glycolic acid polymer, various physical properties (strength, flexability and the like) of the nylon will be impaired, which detracts from the objects of the present invention.

Whether the ester-amide exchange reaction substantially occurs between the nylon and the lactic acid polymer or the glycolic acid polymer or not can be judged, for example, by dissolving the obtained mixture of the nylon and the lactic acid polymer or the glycolic acid polymer in a solvent such as hexafluoroisopropanol or trifluoroethanol, and then measuring nuclear magnetic resonance (NMR).

That is, when the ester-amide exchange reaction does not substantially occur between the nylon and the lactic acid polymer or the glycolic acid polymer, any absorption peaks are not substantially observed in an NMR spectrum except absorption peaks attributable to the nylon, the lactic acid polymer or the glycolic acid polymer which are mixed, and a solvent for the NMR measurement.

The amount of the lactic acid polymer or the glycolic acid polymer which is mixed with the nylon is from 1 to 50 parts by weight, preferably 1 to 10 parts by weight with respect to 100 parts by weight of the nylon. When the amount of the lactic acid polymer or the glycolic acid polymer is more than 50 parts by weight, various characteristics such as mechanical properties and chemical resistance which the nylon has are easily impaired. Conversely, when it is less than 1 part by weight, the hydrolyzability of the nylon cannot be effectively increased.

In the present invention, the polylactic acid, the polyglycolic acid or lactic acid-glycolic acid copolymer can be more preferably used. They comprise the lactic acid unit and/or the glycolic acid unit alone, and therefore the hydrolyzability of the nylon can be effectively increased by a relatively small amount of this polymer, and in this case, various characteristics such as mechanical properties and chemical resistance which the nylon inherently has are not impaired.

As a method of mixing the nylon with the lactic acid polymer or the glycolic acid polymer, there are a mixing process which comprises dissolving the nylon and the lactic acid polymer on the glycolic acid polymer in a solvent such as trifluoroethanol or hexafluoroisopropanol in which both the polymers are soluble, or another mixing process which comprises melting and mixing the nylon and the lactic acid polymer or the glycolic acid polymer in a temperature range of melting points or glass transition points or more of both the polymers to 300° C. The latter process ca be preferably carried out. When the mixing temperature is in excess of 300° C., the lactic acid polymer or the glycolic acid polymer thermally decomposes unpreferably. The mixing temperature is preferably in the range of 170° to 300° C., more preferably 220° to 270° C.

For the melting/mixing, a known device can be used, and examples of the melting/mixing technique include a mixing manner by a kneader using Brabender Plastograph, a mixing manner by a single-screw or a twin-screw melting extruder, and a kneading manner by heating rolls.

It is preferred that the nylon and the lactic acid polymer or the glycolic acid polymer are sufficiently dried prior to the mixing. For the drying, a known method can be applied, and examples of the drying method include a drying manner by heating, a drying method under reduced pressure and a drying manner by heating under reduced pressure. In the case of the drying manner with the heating, the drying step is preferably carried out at a temperature of 150° C. or less. When the drying temperature is in excess of 150° C., the lactic acid polymer or the glycolic acid polymer decomposes at times unpreferably.

In the case that the nylon with the lactic acid polymer or the glycolic acid polymer are melted and mixed, a heating/melting time (which is a residence time in the case of the continuous melting/mixing) is preferably less than 30 minutes. When the heating/melting time is in excess of 30 minutes, the ester-amide exchange reaction easily occurs and the molecular weight of the nylon decreases unpreferably. More preferably, the heating-/melting time is less than 10 minutes.

In the case that the nylon is mixed with the lactic acid polymer or the glycolic acid polymer in the above-mentioned manner, they may take the form of powders, pellets or beads.

No particular restriction is put on a process for molding the mixture of the nylon and the lactic acid polymer or the glycolic acid polymer obtained by the above-mentioned manner, and for example, the mixture can be molded into films, sheets, containers, rods, gears, bolts, nuts or the like by a known process such as a solution rolling manner, a screw melting/extruding manner, an injection molding manner or a calender molding manner. Alternatively, the mixture can be spun into threads in a known manner.

In general, it can easily presumed that after the mixture of the nylon and the lactic acid polymer or the glycolic acid polymer is disposed of, the lactic acid polymer on the glycolic acid polymer having the hydrolyzability contained in the mixture will be hydrolyzed by water in environments.

Under mild conditions such as the natural environments, the hydrolyzability of the nylon ought to be extremely low. However, according to the present invention, the nylon can be suprisingly effectively decomposed in the case that it is physically mixed with the lactic acid polymer or the glycolic acid polymer. This fact can be easily confirmed. That is, when the nylon with the lactic acid polymer or the glycolic acid polymer are melted and mixed and the resultant mixture is then allowed to stand in water, the molecular weight of the nylon itself decreases in a relatively short time, and strength is remarkably lost.

In addition, the above-mentioned effect can be achieved by a relatively small amount of the lactic acid polymer or the glycolic acid polymer which is mixed with the nylon. Therefore, when the above-mentioned mixture is used as the raw material of the molded articles, various advantageous characteristics such as mechanical strength which the nylon inherently has are not noticeably impaired.

In applying the present invention, it is preferred that the nylon is mixed with the lactic acid polymer or the glycolic acid polymer and the resultant mixture is then molded, when the molded articles of the nylon or its composition are used as throwaway products. In the case that they are used as durable products, the molded articles of the nylon or its composition are preferably mixed with the lactic acid polymer or the glycolic acid polymer prior to the disposal.

In addition to the lactic acid polymer or the glycolic acid polymer, some additives can be added to the nylon, as long as they do not impair the objects of the present invention. Examples of the additives include a filler such as calcium carbonate, barium sulfate, silica or carbon black, a lubricant such as steric acid or calcium stearate, an ultraviolet absorber, a pigment, a dye and a stabilizer.

Now, the present invention will be described in more detail in reference to examples and comparative examples. The molecular weight of each polymer in the examples was measured by gel permeation chromatography (GPC). As a solvent, hexafluoroisopropanol (HFIP) was used.

PREPARATION EXAMPLE 1 (SYNTHESIS OF POLYLACTIC ACID)

100 g of L-lactide, 0.005 g of stannous octoate and 0.1 g of lauryl alcohol were placed in a glass reactor, and the atmosphere in the reactor was replaced with nitrogen. Afterward, they were allowed to react at 180° C. for 4 hours. The resultant reaction product was dissolved in 500 g of chloroform, and 2 liters of methanol were poured thereinto with stirring. The formed precipitate was recovered and then dried under reduced pressure to obtain polylactic acid (hereinafter referred to as "PLLA1"). According to measurement by GPC, the weight average molecular weight of this polymer was 85000.

PREPARATION EXAMPLE 2 (SYNTHESIS OF POLYLACTIC ACID)

The same procedure as in Preparation Example 1 was effected except that 100 g of DL-lactide and 0.3 g of lauryl alcohol were used, thereby obtaining polylactic acid (hereinafter referred to as "PLLA2"). According to measurement by GPC, the weight average molecular weight of this PLLA2 was 36000.

PREPARATION EXAMPLE 3 (SYNTHESIS OF GLYCOLIC ACID-LACTIC ACID COPOLYMER)

1161 g (10 mols) of glycolide and 1441 g (10 mols) of L-lactide were placed in a glass reactor, and 10 ml of a toluene solution containing 0.26 g of stannous octoate and 9.0 g of lauryl alcohol were added to the reactor. Afterward, deaeration was carried out for 2 hours under reduced pressure, and the atmosphere in the reactor was then replaced with a nitrogen gas. This mixture was heated at 220° C. for 2 hours with stirring under the nitrogen atmosphere. While the temperature was maintained as it was, the deaeration was slowly preformed by means of a vacuum pump through an exhaust pipe to reduce the pressure in the reactor to 3 mm Hg. One hour after the start of the deaeration, the monomers and low-molecular substances were not extracted any more, and the interior of the reactor was replaced with nitrogen and a resultant glycolic acid-lactic acid copolymer (hereinafter referred to as "PLGA") was then taken out.

This PLGA was transparent and substantially colorless and had a weight average molecular weight of 51000. Furthermore, according to measurement from an H-NMR spectrum, a molar ratio of a glycolic acid unit to a lactic acid unit in the copolymer was 51 to 49.

PREPARATION EXAMPLE 4 (SYNTHESIS OF LACTIC ACID-HYDROXYCAPROIC ACID COPOLYMER)

The same procedure as in Preparation Example 3 was effected except that 1441 g (10 mols) of L-lactide, 1140 g (10 mols) of ε-caprolactone and 10 ml of a toluene solution containing 0.26 g of stannous octoate, and 5 g of lauryl alcohol were used and that reaction was carried out at 160° C. for 10 hours, thereby obtaining a lactic acid-hydroxycaproic acid copolymer (hereinafter referred to as "PCLA1").

This PCLA1 was transparent and substantially colorless and had a weight average molecular weight of 63000. Furthermore, according to measurement from an H-NMR spectrum, a molar ratio of a lactic acid unit to a hydroxycaproic acid unit in the copolymer was 52 to 48.

PREPARATION EXAMPLE 5 (SYNTHESIS OF POLYGLYCOLIC ACID)

The same procedure as in Preparation Example 3 was effected except that 2 kg (17.2 mols) of glycolide and 10 ml of a toluene containing 0.06 g of stannous octoate, and 5.4 g of lauryl alcohol were used and that reaction was carried out at 230°-235° C. for 2 hours thereby obtaining a polyglycolic acid (hereinafter referred to as "PGA"). This PGA was substantially colorless and had a weight average molecular weight of 95000.

PREPARATION OF EXAMPLE 6 (SYNTHESIS OF POLYESTERAMIDE)

Poly[oxysuccinoloxyhexane-1,6-di(amidocarbonylmethylene)] was obtained in accordance with the same procedure as disclosed in U.S. Pat. No. 4,343,931. This polyesteramide (hereinafter referred to as "PEA") had an intrinsic viscosity of 1.12 (which was measured at 30° C. at a concentration of 0.5 % by weight in 2,2,2-trifluoroethanol). This PEA was a copolymer containing 40 mol % of a glycolic acid unit, as was apparent from the manufacturing process.

PREPARATION EXAMPLE 7 (SYNTHESIS OF LACTIC ACID-HYDROXYCAPROIC ACID COPOLYMER)

The same procedure as in Preparation Example 4 was effected except that 6 mols of L-lactide and 14 mols of ε-caprolactone were used, thereby obtaining a lactic acid-hydroxycaproic acid copolymer (hereinafter referred to as "PCLA2"). This PCLA2 had a weight average molecular weight of 72000, and a molar ratio of a lactic acid unit to a hydroxycaproic acid unit in the copolymer was 33 to 67.

EXAMPLES 1 TO 6

Pellets of commercially available 6-nylon or 6,6-nylon were dried at a temperature of 80° C. under a reduced pressure of 5 mm Hg for 20 hours. These nylon pellets were mixed with each of various lactic acid polymers (PLLA1, PLLA2, PLGA and PCLA1) obtained in Preparation Examples 1 to 4 in weight ratios shown in Table 1, and each mixture was then extruded and pelletized, while melted and kneaded at 240° C. (in Example 6 at 270° C.) by the use of a twin-screw type kneader of model KRC made by Kurimoto Co., Ltd. (residence time about 5 minutes).

The thus obtained pellets were then melted and extruded at 240° C. (in Example 6, at 270° C.) in a winding ratio of 10 by the use of a 10 mm screw type extruder equipped with a nozzle for spinning to obtain monofilaments. Each monofilament had a diameter of 0.3 mm.

Part of the filaments obtained in Examples 1 to 4 were dissolved in hexafluoroisopropanol (concentration about 10% by weight), and about 1% by weight of chloroform deuteride was added to the solution. Afterward, each NMR spectrum was measured by the use of a 25 MHz carbon NMR apparatus.

As a result, in Examples 1 to 4, there were six absorption peaks at 26.9 ppm, 27.7 ppm, 30.0 ppm, 38.0 ppm, 41.7 ppm and 178.9 ppm attributed to the 6-nylon; three absorption peaks at 16.7 ppm, 69.0 ppm and 169.6 ppm (they were all singlet peaks) attributed to a polylactic acid; and a peak attributed to hexafluoroisopropanol. Absorption peaks whose derivation was indefinite were not substantially observed.

Next, a plurality of the filaments obtained in Examples 1 to 6 were placed in a phosphoric acid buffer solution having a pH of 7.0 maintained at 60° C., and they were then treated for a period of time shown in Table 1. Afterward, they were taken out one by one, and tensile strength was measured in accordance with a procedure described in JIS L-1013 by means of a tensile testing machine.

The respective filaments rapidly lost strength, and after about 2 weeks, the strength deteriorated so noticeably that its measurement was difficult. The obtained results are set forth in Table 1.

Furthermore, the respective filaments which had been immersed in the phosphoric acid buffer solution were dissolved in HFIP, and weight average molecular weight (Mw) and number average molecular weight (Mn) were measured by GPC. The molecular weight of the filaments gradually deteiorated, which indicated that the nylon was effectively hydrolyzed. The obtained results are set forth in Table 1.

COMPARATIVE EXAMPLE 1

The same procedure as in Example 1 was effected except that any lactic acid polymer was not mixed, thereby molding 6-nylon into monofilaments. The thus obtained filaments were treated in the same manner as in Example 1 by the use of a phosphoric acid buffer solution having a pH of 7.0, and tensile properties and molecular weight were measured in the same manner as in Example 1. The results are set forth in Table 2.

COMPARATIVE EXAMPLES 2 TO 5

The same procedure as in Example 1 was effected except that lactic acid polymer was replaced with polybutylene terephthalate shown in Table 2 [made by Toray Industries, Inc.; spinning grade; hereinafter referred to as "PBT") and that PEA obtained in Preparation Example 6 or PCLA2 obtained in Preparation Example 7 was used in ratios shown in Table 2, thereby obtaining filaments. These filaments obtained in Comparative Examples 2 to 5 were remarkably different from the filaments of 6-nylon obtained in Comparative Example 1 in points of appearance, softness, strength and elongation.

The thus obtained filaments were treated in the same manner as in Example 1 by the use of a phosphoric acid buffer solution having a pH of 7.0, and tensile properties and molecular weight were then measured.

Even when 43 parts by weight of PBT were mixed with 100 parts by weight of 6-nylon (Comparative Example 3), molecular weight, tensile properties and the like after 30 days were not substantially changed as compared with the filaments before the hydrolysis treatment. The obtained results are set forth in Table 2.

EXAMPLES 7 TO 9

The same procedure as in Example 1 was effected except that commercially available 6-nylon and PGA obtained in Preparation Example 5 were mixed in weight ratios shown in Table 3, thereby obtaining monofilaments.

Part of the thus obtained filaments were dissolved in hexafluoroisopropanol, and NMR spectra were measured in the same manner as in Example 1. In every example, there were six absorption peaks at 26.9 ppm, 27.7 ppm, 30.0 ppm, 38.0 ppm, 41.7 ppm, and 178.9 ppm attributed to the 6-nylon; two absorption peaks at 62.0 ppm and 169.2 ppm (they were all singlet peaks) attributed to PGA; and a peak attributed to hexafluoroisopropanol. Absoprtion peaks whose derivation was indefinite were not substantially observed.

Next, the obtained filaments were treated in a phosphoric acid buffer solution having a pH of 7.0 in the same manner as in Example 1, and afterward, they were taken out one by one at predetermined times shown in Table 3 and tensile strength was then measured by means of a tensile testing machine.

After 5 days, the filaments rapidly lost strength. The obtained results are set forth in Table 3.

TABLE 1

| Composition Weight Ratio | | Immersion Days (60° C.) 0 | 6 | 14 | 23 | 30 |
|---|---|---|---|---|---|---|
| Example 1 | | | | | | |
| 6-Nylon/ | Tensile Strength (MPa) | 72 | 29 | 8 | — | — |
| PLLA1 | Elongation (%) | 491 | 6 | 3 | — | — |
| 100/2 | Elastic Modulus (GPa) | 1.70 | 1.09 | 0.81 | — | — |
| | Mw | 29600 | 17900 | 11200 | 8200 | 7600 |
| | Mn | 13200 | 7600 | 4200 | 2300 | 1800 |
| Example 2 | | | | | | |
| 6-Nylon/ | Tensile Strength (MPa) | 70 | 30 | 15 | 3 | — |
| | Elongation (%) | 290 | 5 | 2 | — | — |
| 100/5 | Elastic Modulus (GPa) | 1.66 | 1.49 | 1.00 | — | — |
| | Mw | 28900 | 23200 | 19800 | 14800 | 12500 |
| | Mn | 12500 | 9600 | 7600 | 4600 | 2700 |
| Example 3 | | | | | | |
| 6-Nylon/ | Tensile Strength (MPa) | 63 | 35 | 11 | — | — |
| PLLA2 | Elongation (%) | 552 | 7 | 2 | — | — |
| 100/11 | Elastic Modulus (GPa) | 1.66 | 1.21 | 0.74 | — | — |
| | Mw | 29300 | 21900 | 16500 | 10200 | 5400 |
| | Mn | 10700 | 8400 | 6200 | 3500 | 1400 |
| Example 4 | | | | | | |
| 6-Nylon/ | Tensile Strength (MPa) | 61 | 33 | 12 | — | — |
| PLLA2 | Elongation (%) | 597 | 12 | 2 | — | — |
| 100/43 | Elastic Modulus (GPa) | 1.77 | 1.88 | 0.82 | — | — |
| | Mw | 31800 | 21200 | 14300 | 9800 | 4900 |
| | Mn | 13300 | 8500 | 5500 | 3000 | 1100 |
| Example 5 | | | | | | |
| 6-Nylon/ | Tensile Strength (MPa) | 65 | 21 | 4 | — | — |
| PLGA | Elongation (%) | 520 | 5 | 2 | — | — |
| 100/10 | Elastic Modulus (GPa) | 1.84 | 1.13 | 0.64 | — | — |
| | Mw | 31600 | 16800 | 12600 | 9900 | 9100 |
| | Mn | 14200 | 6900 | 4400 | 3900 | 2400 |
| Example 6 | | | | | | |
| 6,6-Nylon/ | Tensile Strength | 72 | 51 | 29 | 13 | — |

TABLE 1-continued

| Composition Weight Ratio | | Immersion Days (60° C.) 0 | 6 | 14 | 23 | 30 |
|---|---|---|---|---|---|---|
| | (MPa) | | | | | |
| PCLA1 | Elongation (%) | 116 | 21 | 9 | 4 | — |
| 100/10 | Elastic Modulus (GPa) | 2.16 | 1.81 | 1.24 | 0.68 | — |
| | Mw | 33500 | 29200 | 21600 | 14800 | 11000 |
| | Mn | 15200 | 13800 | 9900 | 6300 | 3600 |

TABLE 2

| Composition Weight Ratio | | Immersion Days (60° C.) 0 | 6 | 14 | 23 | 30 |
|---|---|---|---|---|---|---|
| Comp. Ex. 1 | | | | | | |
| 6-Nylon | Tensile Strength (MPa) | 73 | 75 | 70 | 62 | 65 |
| 100 | Elongation (%) | 597 | 280 | 290 | 230 | 314 |
| | Elastic Modulus (GPa) | 1.77 | 2.06 | 1.59 | 1.68 | 1.71 |
| | Mw | 31500 | 28600 | 31000 | 28000 | 29400 |
| | Mn | 13700 | 12000 | 11900 | 11300 | 12100 |
| Comp. Ex. 2 | | | | | | |
| 6-Nylon | Tensile Strength (MPa) | 44 | 52 | 56 | 51 | 42 |
| PBT | Elongation (%) | 510 | 6 | 6 | 28 | 24 |
| 100/11 | Elastic Modulus (GPa) | 1.83 | 1.80 | 1.79 | 1.68 | 1.70 |
| | Mw | 33000 | 32100 | 30900 | 31800 | 31500 |
| | Mn | 14700 | 13600 | 12100 | 12000 | 11900 |
| Comp. Ex. 3 | | | | | | |
| 6-Nylon/ | Tensile Strength (MPa) | 53 | 57 | 49 | 61 | 44 |
| PBT | Elongation (%) | 292 | 459 | 314 | 330 | 190 |
| 100/43 | Elastic Modulus (GPa) | 2.26 | 1.56 | 1.67 | 1.81 | 1.59 |
| | Mw | 30500 | 31000 | 29800 | 30000 | 29300 |
| | Mn | 12600 | 11900 | 11700 | 11000 | 11600 |
| Comp. Ex. 4 | | | | | | |
| 6-Nylon/ | Tensile Strength (MPa) | 48 | 53 | 51 | 48 | 50 |
| PEA | Elongation (%) | 360 | 21 | 13 | 9 | 14 |
| 100/25 | Elastic Modulus (GPa) | 1.88 | 1.68 | 1.77 | 1.71 | 1.63 |
| | Mw | 28000 | 29100 | 26500 | 27500 | 26800 |
| | Mn | 11600 | 11900 | 10300 | 10600 | 10100 |
| Comp. Ex. 5 | | | | | | |
| 6-Nylon/ | Tensile Strength (MPa) | 36 | 42 | 38 | 33 | 29 |
| PCLA2 | Elongation (%) | 720 | 360 | 293 | 330 | 180 |
| 100/30 | Elastic Modulus (GPa) | 0.88 | 1.15 | 1.22 | 1.38 | 1.10 |
| | Mw | 34200 | 31000 | 32300 | 29400 | 30600 |

TABLE 2-continued

| Composition Weight Ratio | | Immersion Days (60° C.) 0 | 6 | 14 | 23 | 30 |
|---|---|---|---|---|---|---|
| | Mn | 15900 | 13400 | 12000 | 11300 | 10900 |

TABLE 3

| | Composition | Weight Ratio | | Immersion Days (60° C.) 0 | 5 |
|---|---|---|---|---|---|
| Example 7 | 6-Nylon/ PGA | 100/5 | Tensile Strength (MPa) | 69 | 11 |
| | | | Elongation (%) | 441 | 4 |
| | | | Elastic Modulus (GPa) | 1.69 | 0.89 |
| Example 8 | 6-Nylon/ PGA | 100/11 | Tensile Strength (MPa) | 64 | 8 |
| | | | Elongation (%) | 350 | 2 |
| | | | Elastic Modulus (GPa) | 1.78 | 0.63 |
| Example 9 | 6-Nylon/ PGA | 100/43 | Tensile Strength (MPa) | 59 | 5 |
| | | | Elongation (%) | 322 | 3 |
| | | | Elastic Modulus (GPa) | 1.85 | 0.69 |

What is claimed is:

1. A nylon composition having increased hydrolyzability which is obtained by physically mixing 100 parts by weight, of a nylon with 1 to 50 parts by weight of at least one polymer selected from the group consisting of polylactic acid, polyglycolic acid and a copolymer containing 50 mol % or more of a lactic acid unit or a glycolic acid unit as a repeating unit in its chain.

2. The nylon composition according to claim 1 wherein the weight average molecular weight of the polylactic acid or the copolymer containing 50 mol % or more of the lactic acid unit is from 150 to 700,000.

3. The nylon composition according to claim 1 wherein the weight average molecular weight of the polyglycolic acid or the copolymer containing 50 mol % or more of the glycolic acid unit is from 150 to 200,000.

4. The nylon composition according to claim 1 wherein the copolymer containing 50 mol % or more of the lactic acid unit or the glycolic acid unit is lactic acid-glycolic acid copolymer.

5. A method for increasing the hydrolyzability of a nylon which comprises the step of physically mixing 100 parts by weight, of a nylon with 1 to 50 parts by weight of at least one polymer selected from the group consisting of polylactic acid, polyglycolic acid and a copolymer containing 50 mol % or more of a lactic acid unit or a glycolic acid unit as a repeating unit in its chain.

6. The method for increasing the hydrolyzability of a nylon according to claim 5 wherein the weight average molecular weight of the polylactic acid or the copolymer containing 50 mol % or more of the lactic acid unit is from 150 to 700,000.

7. The method for increasing the hydrolyzability of a nylon according to claim 5 wherein the weight average molecular weight of the polyglycolic acid or the copolymer containing 50 mol % or more of the glycolic acid unit is from 150 to 200,000.

8. The method for increasing the hydrolyzability of a nylon according to claim 5 wherein the copolymer containing 50 mol % or more of the lactic acid unit or the glycolic acid unit is lactic acid-glycolic acid copolymer.

9. The method for increasing the hydrolyzability of a nylon according to claim 5 wherein the physical mixing is carried out in a temperature range of 170° to 300° C.

* * * * *